(12) United States Patent
Nishibayashi

(10) Patent No.: US 6,589,186 B2
(45) Date of Patent: Jul. 8, 2003

(54) BLOOD-PRESSURE MEASURING APPARATUS

(75) Inventor: Hideo Nishibayashi, Komaki (JP)

(73) Assignee: Colin Corporation, Komaki (JP)

(*) Notice: Subject to any disclaimer, the term of this patent is extended or adjusted under 35 U.S.C. 154(b) by 0 days.

(21) Appl. No.: 10/086,809

(22) Filed: Mar. 4, 2002

(65) Prior Publication Data

US 2003/0069507 A1 Apr. 10, 2003

(30) Foreign Application Priority Data

Oct. 9, 2001 (JP) .................................... 2001-311535

(51) Int. Cl.[7] .................................................. A61B 5/02
(52) U.S. Cl. ............................................ 600/494; 600/490
(58) Field of Search ................................. 600/481, 485, 600/490, 492, 493, 494, 445, 496

(56) References Cited

U.S. PATENT DOCUMENTS 4,727,884 A * 3/1988 Link ........................... 600/494
4,880,013 A * 11/1989 Chio ........................... 600/494
5,339,818 A * 8/1994 Baker et al. .................. 600/490

* cited by examiner

*Primary Examiner*—Max F. Hindenburg
*Assistant Examiner*—Navin Natnithithadha
(74) *Attorney, Agent, or Firm*—Oliff & Berridge, PLC

(57) ABSTRACT

A blood-pressure measuring apparatus including a cuff worn on a body portion of a subject to apply a pressure to the body portion; a changing device which changes the cuff pressure; a determining device which determines a diastolic and mean blood pressure of the subject; a detecting device which detects a cuff pulse wave as an oscillation of the cuff pressure; a pulse-wave-magnitude determining device for operating the changing device; and a systolic-blood-pressure determining device for determining a systolic blood pressure of the subject, based on the determined diastolic and mean blood pressure and the determined minimal, mean, and maximal magnitudes of the cuff pulse wave, according to a fact that the minimal, mean, and maximal magnitudes of the cuff pulse wave correspond to the diastolic, mean, and systolic blood pressure of the subject, respectively.

8 Claims, 7 Drawing Sheets

BLOOD-PRESSURE MEASURING APPARATUS

BACKGROUND OF THE INVENTION

1. Field of the Invention

The present invention relates to a blood-pressure measuring apparatus that measures a blood pressure with an inflatable cuff.

2. Related Art Statement

There is widely known a blood-pressure measuring apparatus that includes an inflatable cuff adapted to be worn on a body portion of a living subject and measures a blood pressure of the subject by slowly changing a pressing pressure of the cuff. The blood-pressure measuring apparatus is operated according to any of various known blood-pressure measuring methods including a microphone method, an oscillometric method, and an ultrasonic Doppler method. In many cases, the pressing pressure of the cuff is slowly decreased to measure a blood pressure but, in some cases, the pressing pressure is slowly increased.

In a conventional blood-pressure measuring apparatus that measures a blood pressure of a living subject with an inflatable cuff, first, a pressing pressure of the cuff is increased up to a target pressure that is estimated to be sufficiently higher than a systolic blood pressure of the subject, so that an artery located under the cuff can be completely occluded. If not, the systolic blood pressure of the subject cannot be measured. Thus, a blood-pressure measurement causes a living subject to feel some pain. In particular, in the case where a blood pressure is measured using an inflatable cuff adapted to be worn on an ankle of a living subject, the subject feels more pain because of having a higher systolic blood pressure at the ankle.

SUMMARY OF THE INVENTION

It is therefore an object of the present invention to provide a blood-pressure measuring apparatus which can measure a systolic blood pressure of a living subject without causing the subject to feel pain.

The above object has been achieved by the present invention according to which there is provided an apparatus for measuring a blood pressure of a living subject, comprising an inflatable cuff which is adapted to be worn on a body portion of the subject and which applies a pressure to the body portion of the subject; a cuff-pressure changing device which changes the pressure of the cuff between a first pressure lower than a systolic blood pressure of the body portion of the subject and higher than a mean blood pressure of the body portion, and a second pressure lower than a diastolic blood pressure of the body portion; a blood-pressure determining device which determines a diastolic blood pressure and a mean blood pressure of the subject based on a heartbeat-synchronous signal which is detected from the subject while the cuff-pressure changing device changes the pressure of the cuff; a cuff-pulse-wave detecting device which detects a cuff pulse wave as an oscillation of the pressure of the cuff; a pulse-wave-magnitude determining means for operating the cuff-pressure changing device to maintain the pressure of the cuff at a third pressure lower than the mean blood pressure of the body portion of the subject, and determining a minimal magnitude, a mean magnitude, and a maximal magnitude of the cuff pulse wave detected by the cuff-pulse-wave detecting device in a state in which the pressure of the cuff is maintained at the third pressure; and a systolic-blood-pressure determining means for determining a systolic blood pressure of the subject, based on the diastolic and mean blood pressure determined by the blood-pressure determining device and the minimal, mean, and maximal magnitudes of the cuff pulse wave determined by the pulse-wave-magnitude determining means, according to a fact that the minimal, mean, and maximal magnitudes of the cuff pulse wave correspond to the diastolic, mean, and systolic blood pressure of the subject, respectively.

According to this invention, the cuff-pressure changing device slowly changes the pressure of the cuff between a pressure lower than a systolic blood pressure of the body portion of the subject and higher than a mean blood pressure of the body portion, and a pressure lower than a diastolic blood pressure of the body portion, and the blood-pressure determining device determines a diastolic blood pressure and a mean blood pressure of the subject based on a heartbeat-synchronous signal detected from the subject during the slow changing of the cuff pressure. In addition, the pulse-wave-magnitude determining means determines a minimal magnitude, a mean magnitude, and a maximal magnitude of a cuff pulse wave detected by the cuff-pulse-wave detecting device in a state in which the cuff pressure is maintained at a pressure lower than the mean blood pressure of the body portion by the cuff-pressure changing device. And, the systolic-blood-pressure determining means determines a systolic blood pressure of the subject, based on the diastolic and mean blood pressure and the minimal, mean, and maximal magnitudes of the cuff pulse wave. Thus, the present apparatus can determine the systolic blood pressure of the subject, without having to increase the cuff pressure up to a pressure higher than the systolic blood pressure. That is, the present apparatus can determine a systolic blood pressure of a patient without having to cause the patient to feel pain.

Preferably, the cuff-pressure changing device increases the pressure of the cuff at a predetermined rate from a start pressure lower than the diastolic blood pressure of the body portion of the subject, and stops the increasing of the pressure of the cuff based on a fact that the blood-pressure determining device has determined the mean blood pressure of the subject. According to this feature, the increasing of the cuff pressure is stopped based on the fact that the blood-pressure determining device has actually determined the mean blood pressure of the subject. Therefore, the cuff pressure has only to be increased up to the lowest possible pressure to determine or estimate the systolic blood pressure. Thus, the pain the patient feels can be reduced.

Preferably, the blood-pressure measuring apparatus further comprises a blood-pressure re-determining means for increasing the pressure of the cuff up to a target pressure higher by a predetermined pressure than the systolic blood pressure determined by the systolic-blood-pressure determining means, subsequently decreasing the cuff pressure at a predetermined rate, and re-determining a systolic blood pressure of the subject based on the heartbeat-synchronous signal detected while the cuff pressure is decreased at the predetermined rate. According to this feature, the cuff pressure is increased up to the target pressure higher than the systolic blood pressure determined by the systolic-blood-pressure determining means, so that an artery located below the cuff is completely occluded and, in this state, a systolic blood pressure is re-determined. Therefore, the re-determined systolic blood pressure enjoys a high accuracy. In addition, since the target pressure is determined based on the systolic blood pressure determined by the systolic-blood-pressure determining means, the thus determined target pressure would be lower, in many cases, than a target pressure which is selected, in the conventional blood-pressure measuring apparatus, at a value sufficiently higher than an average systolic blood pressure. Thus, the pain felt by the patient undergoing the blood-pressure measurement is reduced.

BRIEF DESCRIPTION OF THE DRAWINGS

The above and optional objects, features, and advantages of the present invention will be better understood by reading the following detailed description of preferred embodiments of the invention when considered in conjunction with the accompanying drawings, in which.

DETAILED DESCRIPTION OF PREFERRED EMBODIMENTS

Figure 1:
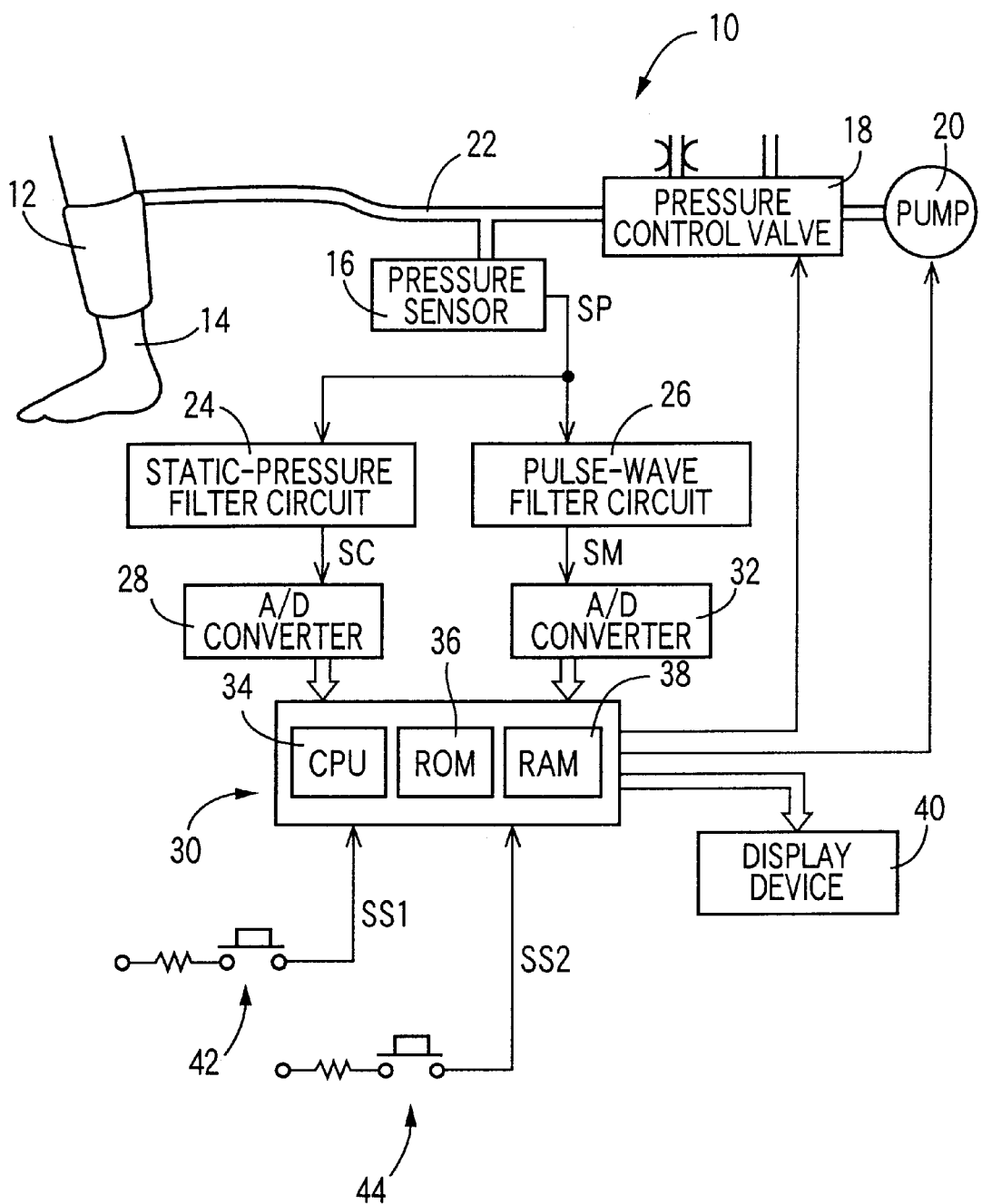
FIG. 1 is a diagrammatic view showing a construction of a blood-pressure measuring apparatus to which the present invention is applied.

Hereinafter, there will be described an embodiment of the present invention, by reference to the drawings. FIG. 1 is a diagrammatic view showing a construction of a blood-pressure measuring apparatus 10 to which the present invention is applied. The present apparatus includes a common ankle cuff which includes a belt-like cloth bag and a rubber bag accommodated in the cloth bag and which is wound around an ankle 14 of a right leg of a living subject. The cuff 12 is connected to a pressure sensor 16, a pressure control valve 18, and an air pump 20 via a piping 22. The pressure control valve 18 includes a valve member, and is electrically operable to change an opening angle of the valve member. The pressure control valve 18 decreases, according to the current opening angle of the valve member, a pressure of a pressurized air supplied from the air pump 20, to an arbitrary pressure with which the pressurized air is supplied to the cuff 12. This is performed when the pressure control valve 18 is placed in a pressure-supply position thereof. The pressure control valve 18 is selectively placed in the pressure-supply position, a slow-deflation position thereof in which the opening angle of the valve member of the pressure control valve 18 is so changed as to permit the pressurized air to be slowly discharged at a prescribed rate from the cuff 12, and a quick-deflation position thereof in which the pressure control valve 18 permits the pressurized air to be quickly discharged from the cuff 12.

The pressure sensor 16 detects an air pressure $P_K$ in the cuff 12, and supplies a pressure signal SP representing the detected pressure $P_K$, to each of a static-pressure filter circuit 24 and a pulse-wave filter circuit 26. The static-pressure filter circuit 24 includes a low-pass filter and extracts, from the pressure signal SP, a static-pressure component contained in the pressure signal SP, i.e., a cuff-pressure signal SC representing the static or pressing pressure in the cuff 10 (hereinafter, referred to as the cuff pressure, Pc). The cuff-pressure signal SC is supplied to an electronic control device 30 via an A/D (analog-to-digital) converter 28. The pulse-wave filter circuit 26 includes a band-pass filter and extracts, from the pressure signal SP, an oscillating component that is produced in synchronism with heartbeats of a patient, i.e., a cuff-pulse-wave signal SM. The cuff-pulse-wave signal SM is supplied to the control device 30 via an A/D converter 32. The cuff-pulse-wave signal SM represents a cuff pulse wave, CW, i.e., a pressure pulse wave that is produced in the ankle 14 and is propagated to the cuff 12. The cuff pulse wave CW is a sort of heartbeat-synchronous signal. The pulse-wave filter circuit 26 functions as a cuff-pulse-wave detecting device.

The control device 30 is provided by a so-called microcomputer including a CPU (central processing unit) 34, a ROM (read only memory) 36, a RAM 38, and an I/O port, not shown. The CPU 34 processes signals according to the control programs pre-stored in the ROM 36 by utilizing the temporary-storage function of the RAM 38, and controls the pressure control valve 18 and the air pump 20 by outputting respective drive signals to respective drive circuits, not shown, via the I/O port. Thus, the CPU 34 controls the pressure in the cuff 12. In addition, the CPU 34 determines, based on the signals supplied to the control device 30, a blood-pressure value BP of the patient, and controls a display device 40 to display the thus determined blood-pressure value BP.

A first-measurement start button 42 supplies, when being pushed or operated, a first-measurement start signal, SS1, to the control device 30, so as to start a first blood-pressure measurement in which a blood-pressure value of the patient is measured without increasing the cuff pressure Pc up to a systolic blood-pressure value BP(SYS) of the patient. A second-measurement start button 44 supplies, when being pushed or operated, a second-measurement start signal, SS2, to the control device 30, so as to start a second blood-pressure measurement in which a blood-pressure value of the patient is measured by increasing the cuff pressure Pc up to a pressure higher than a systolic blood-pressure value BP(SYS) of the patient.

Figure 2:
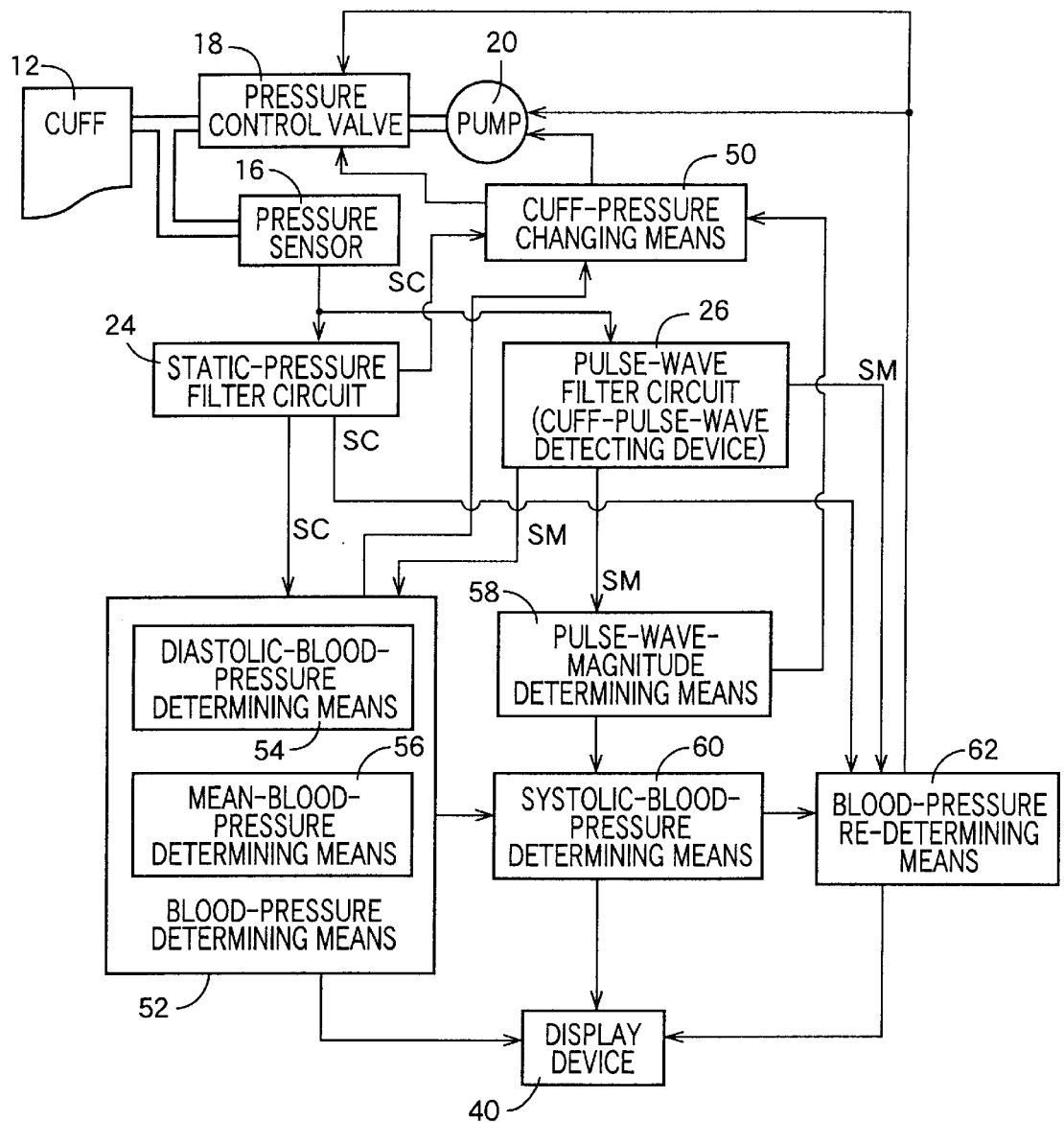
FIG. 2 is a block diagram for explaining essential control functions of an electronic control device of the apparatus of FIG. 1.
Figure 3:
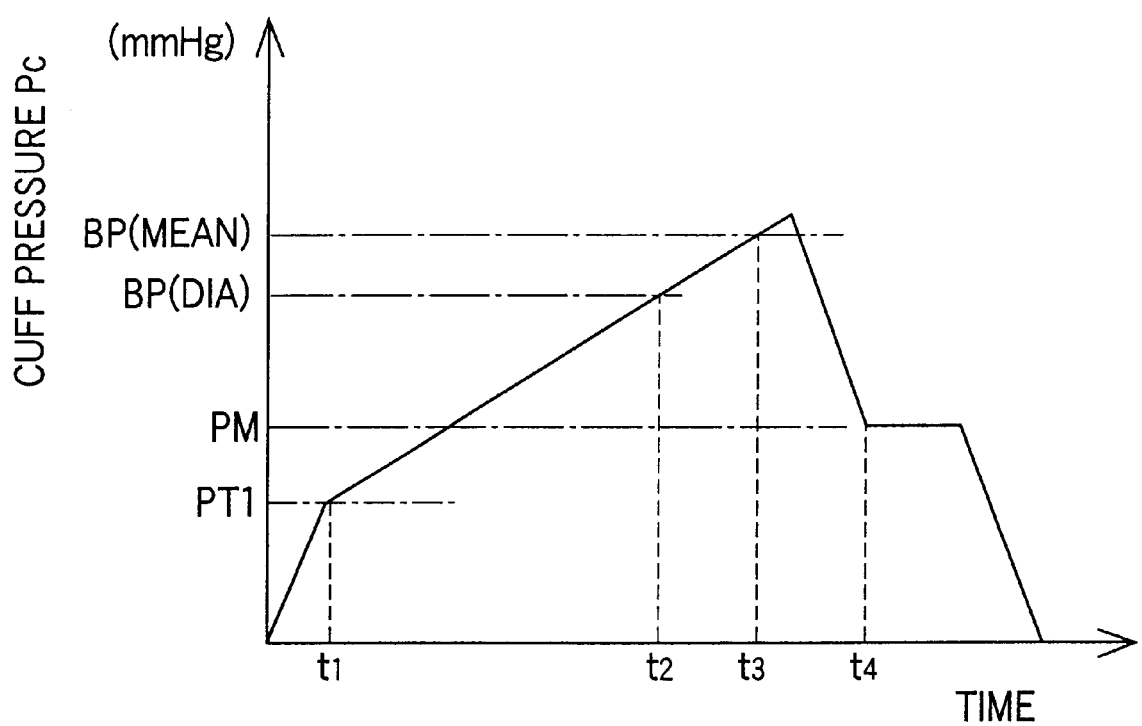
FIG. 3 is a time chart showing a manner in which a cuff-pressure changing means shown in FIG. 2 changes a cuff pressure, Pc.

FIG. 2 is a block diagram for explaining essential functions of the control device 30. When the first-measurement start button 42 supplies the first-measurement start signal SS1 to the control device 30, a cuff-pressure changing means 50 recognizes the cuff pressure Pc from the cuff-pressure signal SC supplied from the static-pressure filter circuit 24, and operates the air pump 20 and the pressure control valve 18 to quickly increase the cuff pressure Pc up to a prescribed slow-pressure-increase start pressure, PT1, (e.g., 40 mmHg) that is sufficiently lower than an average diastolic blood-pressure value of a body portion of a human person on which a cuff is worn, e.g., the ankle 14 of the patient on which the cuff 12 is worn, and subsequently increase the cuff pressure Pc linearly at a prescribed low rate (e.g., 3 mmHg/sec). During this slow inflation of the cuff 12, a diastolic-blood-pressure determining means 54, described later, determines a diastolic blood-pressure value, BP(DIA), of the patient and a mean-blood-pressure determining means 56, described later, determines a mean blood-pressure value, BP(MEAN), of the patient. The cuff-pressure changing means 50 determines, as a pulse-wave-detect pressure, PM, a pressure lower by a prescribed pressure, a, than the thus determined diastolic blood-pressure value BP(DIA) or mean blood-pressure value BP(MEAN), and immediately decreases the cuff pressure Pc down to the thus determined pulse-wave-detect pressure PM and maintains the pressure PM. Thus, a pulse-wave-magnitude determining means 58, described later, determines a magnitude, I, of the cuff pulse wave CW. Then, the cuff-pressure changing means 50 decreases the cuff pressure Pc down to an atmospheric pressure. FIG. 3 shows a time chart showing a manner in which the cuff-pressure changing means 50 changes the cuff pressure Pc.

The pulse-wave-detect pressure PM is so determined as to assure that a waveform of the cuff pulse wave CW is substantially identical with a waveform of pulsation of blood pressure in an artery underlying the cuff 12. If the cuff pressure Pc is higher than the mean blood-pressure value BP(MEAN), the waveform of the cuff pulse wave CW is deformed and does not reflect the waveform of the arterial pulsation under the cuff 12. Thus, the pulse-wave-detect pressure PM is determined as being lower than the mean blood-pressure value BP(MEAN). In order that the waveform of the cuff pulse wave CW may more accurately reflect the waveform of the arterial pulsation under the cuff 12, it is preferred that the pulse-wave-detect pressure PM be lower than the diastolic blood-pressure value BP(DIA). However, if the pulse-wave-detect pressure PM is too low, the cuff-pulse-wave signal SM obtained becomes too weak. In order that the cuff-pulse-wave signal SM may be sufficiently strong, it is preferred that the prescribed pressure α be a considerably small value.

A blood-pressure determining means 52 includes the diastolic-blood-pressure determining means 54 and the mean-blood-pressure determining means 56. The diastolic-blood-pressure determining means 54 determines, by using a well-known oscillometric algorithm, the diastolic blood-pressure value BP(DIA), based on the cuff pulse wave CW continuously detected while the cuff pressure Pc is slowly increased by the cuff-pressure changing means 50. More specifically described, the diastolic-blood-pressure determining means 54 determines, according to the oscillometric algorithm, an envelope of respective amplitudes, A, of respective heartbeat-synchronous pulses of the cuff pulse wave CW, determines a differentiated waveform or curve of the thus determined envelope, and determines, as the diastolic blood-pressure value BP(DIA), a cuff pressure Pc at a time when the differentiated curve shows an inflection point. An amplitude A of a heartbeat-synchronous pulse of the cuff pulse wave CW is defined as a difference between a maximal and a minimal magnitude of the heartbeat-synchronous pulse.

The mean-blood-pressure determining means 56 also determines, by using the well-known oscillometric algorithm, the mean blood-pressure value BP(MEAN), based on the cuff pulse wave CW continuously detected while the cuff pressure Pc is slowly increased by the cuff-pressure changing means 50. More specifically described, the mean-blood-pressure determining means 56 determines, according to the oscillometric algorithm, an envelope of respective amplitudes A of respective heartbeat-synchronous pulses of the cuff pulse wave CW, and determines, as the mean blood-pressure value BP(MEAN), a cuff pressure Pc at a time when the envelope shows a peak, i.e., the greatest amplitude. In addition, the blood-pressure determining means 52 controls the display device 40 to display the thus determined diastolic and mean blood-pressure values BP(DIA), BP(MEAN).

Figure 4:
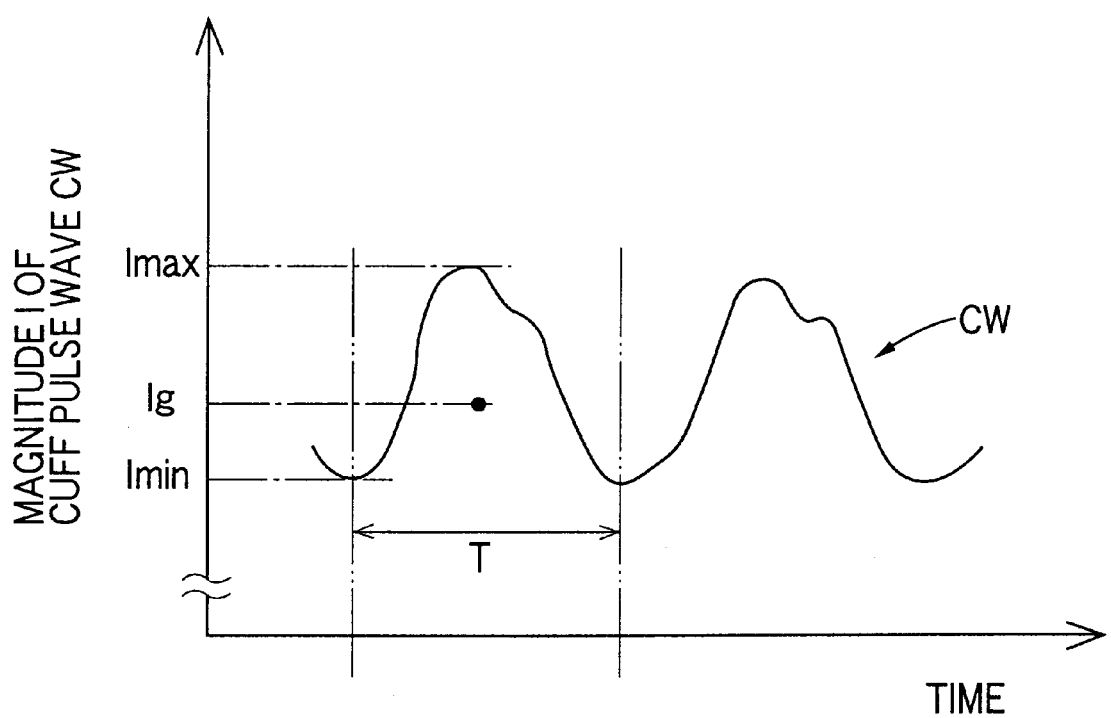
FIG. 4 is a graph showing an example of a cuff pulse wave, CW, which is extracted by a pulse-wave filter circuit shown in FIG. 1.

The pulse-wave-magnitude determining means 58 determines a minimal magnitude, Imin, a mean (i.e., area-gravity-center) magnitude, Ig, and a maximal magnitude, Imax, of the cuff pulse wave CW represented by the cuff-pulse-wave signal SM that is supplied from the pulse-wave filter circuit 26 in the state in which the cuff pressure Pc is maintained at the pulse-wave-detect pressure PM by the cuff-pressure changing means 50. FIG. 4 shows a minimal magnitude Imin, a mean magnitude Ig, and a maximal magnitude Imax, of one heartbeat-synchronous pulse of the cuff pulse wave CW. The mean, i.e., area-gravity-center magnitude Ig may be determined by summarizing a waveform of the one heartbeat-synchronous pulse of the cuff pulse wave CW and dividing the thus summarized value by a period, T, of the one pulse. Alternatively, the minimal magnitude Imin, the mean magnitude Ig, and the maximal magnitude Imax of the cuff pulse wave CW may be an average of respective minimal magnitudes Imin of two or more heartbeat-synchronous pulses of the cuff pulse wave CW, an average of respective mean magnitudes Ig of the two or more heartbeat-synchronous pulses, and an average of respective maximal magnitudes Imax of the two or more heartbeat-synchronous pulses, respectively. Moreover, the minimal magnitude Imin and the maximal magnitude Imax of the cuff pulse wave CW may be the smaller or smallest one of respective minimal magnitudes Imin of two or more heartbeat-synchronous pulses of the cuff pulse wave CW, and the greater or greatest one of respective maximal magnitudes Imax of the two or more heartbeat-synchronous pulses, respectively. In each of the above-described, second and third cases, the two or more heartbeat-synchronous pulses of the cuff pulse wave CW may be obtained either according to a prescribed pulse number, or within a prescribed time period.

Figure 5:
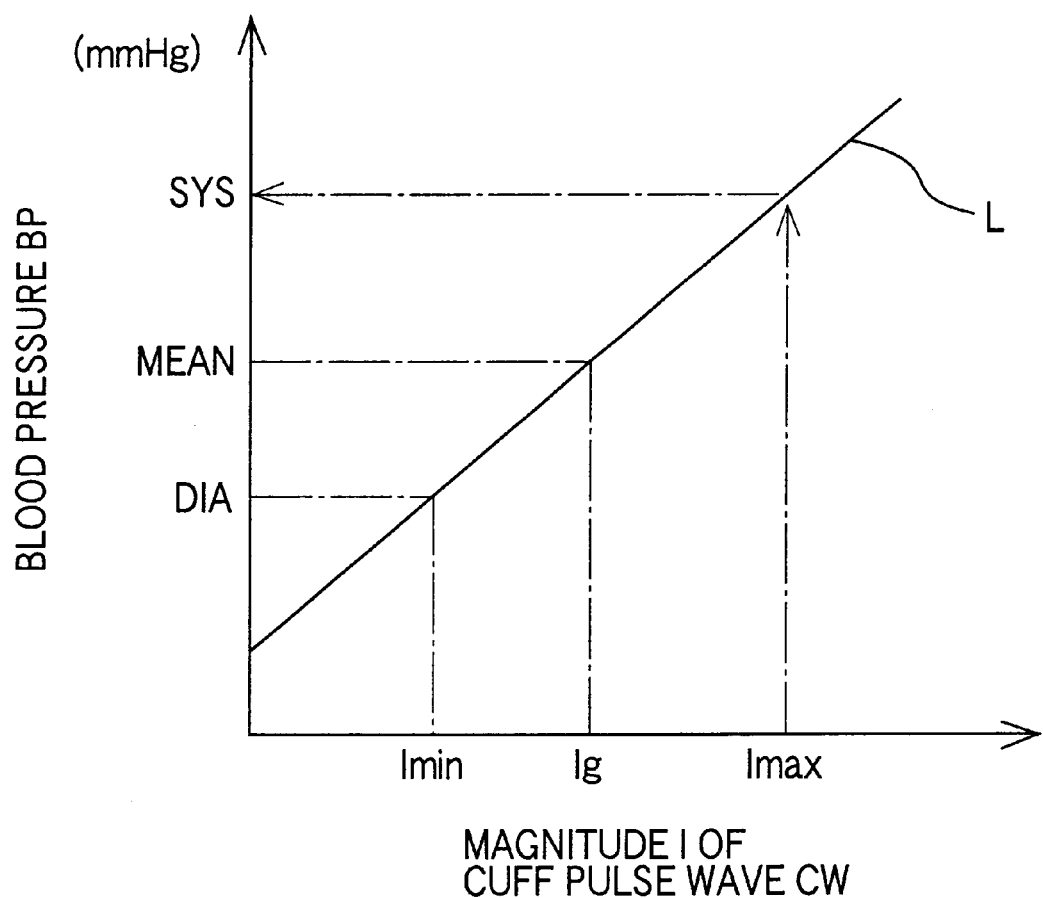
FIG. 5 is a graph showing a relationship, L, between magnitude, I, of cuff pulse wave CW, and blood pressure, BP.

A systolic-blood-pressure determining means 60 determines a systolic blood-pressure value BP(SYS) of a body portion of the patient on which the cuff 12 is worn, based on the diastolic and mean blood-pressure values BP(DIA), BP(MEAN) determined by the blood-pressure determining means 52 and the minimal, mean, and maximal pulse-wave magnitudes Imin, Ig, Imax determined by the pulse-wave-magnitude determining means 58. Since the cuff pulse wave CW is a sort of pressure pulse wave, the minimal and mean magnitudes Imin, Ig of the cuff pulse wave CW correspond to the diastolic and mean blood-pressure values BP(DIA), BP(MEAN), respectively. Therefore, a relationship, L, between magnitude I of cuff pulse wave CW and blood pressure BP, shown in FIG. 5, can be determined based on the diastolic and mean blood-pressure values BP(DIA), BP(MEAN) determined by the blood-pressure determining means 52 and the minimal and mean pulse-wave magnitudes Imin, Ig determined by the pulse-wave-magnitude determining means 58; and a systolic blood-pressure value BP(SYS) can be determined based on the maximal pulse-wave magnitude Imax according to the relationship L. However, the relationship L may not be determined, since the systolic blood-pressure value BP(SYS) can also be determined according to the following Expression 1, Expression 2 obtained from Expression 1, or any other expression equivalent to Expression 1:

$$(Imax-Imin):(Ig-Imin)=\{BP(SYS)-BP(DIA)\}:\{BP(MEAN)-BP(DIA)\} \quad \text{(Expression 1)}$$

$$BP(SYS)=\{(Imax-Imin)\times BP(MEAN)-(Imax-Ig)\times BP(DIA)\}/(Ig-Imin) \quad \text{(Expression 2)}$$

The systolic-blood-pressure determining means 60 controls the display device 40 to display the thus determined systolic blood-pressure value BP(SYS).

A blood-pressure re-determining means 62 is operated when the second-measurement start signal SS2 is supplied from the second-measurement start button 44. Usually, the second-measurement start button 44 is operated by an operator, such as a doctor, when the operator judges, from the systolic blood-pressure value BP(SYS) determined by the systolic-blood-pressure determining means 60 upon operation of the first-measurement start button 42, that it is needed to re-measure a systolic blood-pressure value BP(SYS) in a conventional blood-pressure measuring method.

Thus, usually, at the point of time when the second-measurement start signal SS2 is supplied, the systolic blood-pressure determining means 60 has already determined the systolic blood-pressure value BP(SYS). Therefore, when the second-measurement start signal SS2 is supplied, first, the blood-pressure re-determining means 62 determines, as a pressure-increase target pressure, PT2, a pressure higher by a prescribed pressure, β, than the systolic blood-pressure value BP(SYS) determined by the systolic blood-pressure determining means 60. The pressure β is experimentally determined so that the pressure-increase target pressure PT2 is as low as possible in a range higher than a true systolic blood-pressure value BP(SYS) of the patient. For example, the pressure β may be determined as a value somewhat greater than an error of determination of systolic blood-pressure value BP(SYS) by the systolic blood-pressure determining means 60. In the case where there is no systolic blood-pressure value BP(SYS) that has been determined by the systolic blood-pressure determining means 60, a pre-scribed value (e.g., 240 mmHg), pre-stored in the ROM 36, is employed as the pressure-increase target pressure PT2.

Then, the blood-pressure re-determining means 62 controls the pressure control valve 18 and the air pump 20 to quickly increase the cuff pressure Pc up to the pressure-increase target pressure PT2 and subsequently slowly decrease the cuff pressure Pc at the prescribed low rate (e.g., 3 mmHg/sec). Based on respective amplitudes of respective heartbeat-synchronous pulses of the cuff pulse wave CW represented by the cuff-pulse-wave signal SM continuously obtained during the slow decreasing of the cuff pressure Pc, the re-determining means 62 determines a systolic blood-pressure value BP(SYS) of the patient, according to well-known oscillometric algorithm. Based on those amplitudes, the re-determining means 62 may additionally determine a mean blood-pressure value BP(SYS) and a diastolic blood-pressure value BP(DIA) of the patient. After the re-determining means 62 has determined one or more blood-pressure values BP of the patient, the means 62 decreases the cuff pressure Pc down to the atmospheric pressure, and controls the display device 40 to display the thus determined systolic blood-pressure value BP(SYS), etc.

Figure 6:
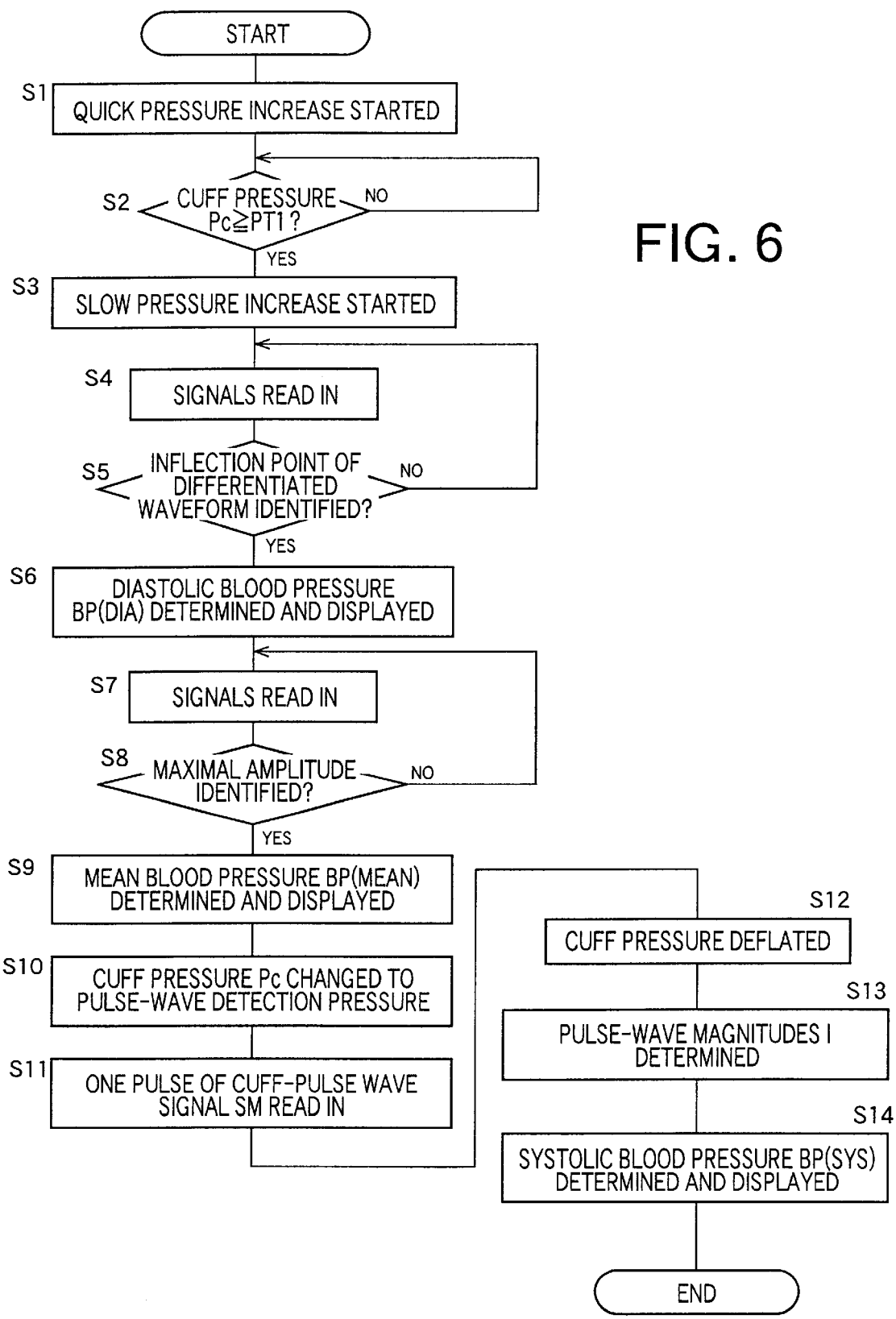
FIG. 6 is a flow chart representing a control program according to which the electronic control device shown in FIG. 2 carries out a first blood-pressure measuring operation.

FIG. 6 is a flow chart for explaining the essential control functions of the control device 30, shown in FIG. 2, that are implemented for carrying out the above-described first blood-pressure measurement, when the first-measurement start button 42 is operated.

First, the control device 30 implements Steps S1 to S3 (hereinafter, "Step(s)" is omitted, if appropriate). At S1, the control device controls the pressure control valve 18 and the air pump 20 to start quick increasing of the cuff pressure Pc. At S2, the control device judges whether the cuff pressure Pc has been increased up to the slow-pressure-increase start pressure PT1 equal to 40 mmHg. S2 is repeated until a positive judgment is made. If a positive judgment is made at S2 (at a time, t1, shown in FIG. 3), the control goes to S3 to control the pressure control valve 18 to slowly increase the cuff pressure Pc at the low rate equal to 3 mmHg/sec. During the slow increasing of the cuff pressure Pc, the control device implements Steps S4 to S9.

Steps S4 and S5 make a loop. At S4, the control device continuously reads in the cuff-pressure signal SC supplied from the static-pressure filter circuit 24 and the cuff-pulse-wave signal SM supplied from the pulse-wave filter circuit 34. At S5, the control device determines respective amplitudes A of respective heartbeat-synchronous pulses of the cuff pulse wave CW represented by the cuff-pulse-wave signal SM read in at S4, determines a differentiated curve of an envelope of those amplitudes A, and judges whether the differentiated curve shows an inflection point. S4 and S5 are repeated until a positive judgment is made at S5. If a positive judgment is made at S5, then the control goes to S6 where the control device determines, as a diastolic blood-pressure value BP(DIA) of the patient, a cuff pressure Pc at a time (i.e., a time, t2, shown in FIG. 3) when the inflection point is shown on the differentiated curve. The thus determined diastolic blood-pressure value BP(DIA) is displayed on the display device 40. S5 and S6 correspond to the diastolic-blood-pressure determining means 54.

Steps S7 and S8 make a loop. At S7 like S4, the control device reads in the cuff-pressure signal SC supplied from the static-pressure filter circuit 24 and the cuff-pulse-wave signal SM supplied from the pulse-wave filter circuit 34. At S8, the control device determines respective amplitudes A of respective heartbeat-synchronous pulses of the cuff pulse wave CW represented by the cuff-pulse-wave signal SM read in at S7, determines an envelope of those amplitudes A, and judges whether the envelope shows a peak, i.e., the greatest amplitude A. S7 and S8 are repeated until a positive judgment is made at S8. If a positive judgment is made at S8, then the control goes to S9 where the control device determines, as a mean blood-pressure value BP(MEAN) of the patient, a cuff pressure Pc at a time (i.e., a time, t3, shown in FIG. 3) when the greatest amplitude A is shown on the envelope. The thus determined mean blood-pressure value BP(MEAN) is displayed on the display device 40. S7 and S8 correspond to the mean-blood-pressure determining means 56.

Then, the control goes to S10 where the control device determines a pulse-wave-detect pressure PM by subtracting, from the diastolic blood-pressure value BP(DIA) determined at S6, the prescribed pressure α equal to 10 mmHg, immediately decreases the cuff pressure Pc down to the pulse-wave-detect pressure PM, and maintains the cuff pressure Pc at the pressure PM (at a time, t4, shown in FIG. 3). Thus, the highest pressure to which the cuff pressure Pc is increased up is sufficiently lower than the systolic blood-pressure value BP(SYS) and is somewhat higher than the mean blood-pressure value BP(MEAN). Then, the control goes to S11 to read in one heartbeat-synchronous pulse of the cuff pulse wave CW represented by the cuff-pulse-wave signal SM, and then goes to S12 to decrease the cuff pressure Pc down to the atmospheric pressure. S1 to S3, S10, and S12 of FIG. 6 correspond to the cuff-pressure changing means 50.

At S13 corresponding to the pulse-wave-magnitude determining means 58, the control device determines a minimal magnitude Imin, a mean magnitude Ig, and a maximal magnitude Imax of the one pulse of the cuff pulse wave CW read in at S11. Then, at S14 corresponding to the systolic-blood-pressure determining means 60, the control device determines a systolic blood-pressure value BP(SYS) of the patient by substituting Expression 2 with the minimal pulse-wave magnitude Imin, the mean pulse-wave magnitude Ig, and the maximal pulse-wave magnitude Imax, determined at S13, and the diastolic blood-pressure value BP(DIA) determined at S6, and the mean blood-pressure value BP(MEAN) determined at S9. The thus determined systolic blood-pressure value BP(SYS) is displayed on the display device 40.

In the illustrated embodiment in which the flow chart shown in FIG. 6 is employed, the control device 30 controls, at S3 to S10 (the cuff-pressure changing means 50), the cuff pressure Pc, i.e., slowly increases the cuff pressure Pc from the slow-pressure-increase start pressure PT1 lower than the diastolic blood-pressure value BP(DIA) of the body portion of the patient on which the cuff 12 is worn, up to the pressure somewhat higher than the mean blood-pressure value BP(MEAN) of the same. At S5, S6, S8, and S9 (the blood-pressure determining means 52), the control device determines the diastolic blood-pressure value BP(DIA) and the mean blood-pressure value BP(MEAN) based on the change of the amplitudes A of the cuff pulse wave CW detected during the slow changing of the cuff pressure Pc. At S13 (the pulse-wave-magnitude determining means 58), the control device determines the minimal magnitude Imin, the mean magnitude Ig, and the maximal magnitude Imax of the cuff pulse wave CW extracted by the pulse-wave filter circuit 26 in the state in which the cuff pressure Pc is maintained at the pulse-wave-detect pressure PM lower than the diastolic blood-pressure value BP(DIA) at S10 (the cuff-pressure changing means 50). At S14 (the systolic-blood-pressure determining means 60), the control device determines, without having to increase the cuff pressure Pc up to a pressure higher than the systolic blood-pressure value BP(SYS), the systolic blood-pressure value BP(SYS) based on the minimal, mean, and maximal magnitudes Imin, Ig, Imax and the diastolic and mean blood-pressure values BP(DIA), BP(MEAN). Thus, the present apparatus 10 can determine the systolic blood-pressure value BP(SYS) of the patient, without giving pain to the patient.

In addition, in the embodiment in which the flow chart shown in FIG. 6 is employed, the control device stops, at S10 (the cuff-pressure changing means 50), the slow increasing of the cuff pressure Pc, based on the mean blood-pressure value BP(MEAN) actually determined at S9 (the mean-blood-pressure determining means 56). Thus, the highest pressure to which the cuff pressure Pc is increased up can be as low as possible, and accordingly the pain felt by the patient can be reduced.

In the illustrated embodiment, when the operator judges, from the systolic blood-pressure value BP(SYS) determined by the systolic-blood-pressure determining means 60, that re-measurement is needed to obtain a more accurate systolic blood-pressure value BP(SYS) of the patient, the operator has only to operate the second-measurement start button 44. In response to the operation of the button 44, the blood-pressure re-determining means 62 increases the cuff pressure Pc up to a pressure higher than the determined systolic blood-pressure value BP(SYS). Thus, the artery underlying the cuff 12 is completely occluded, and accordingly an accurate systolic blood-pressure value BP(SYS) can be determined. In addition, since the pressure-increase target pressure PT2 is determined based on the systolic blood-pressure value BP(SYS) determined by the systolic-blood-pressure determining means 60, the target pressure PT2 can be lower than a target pressure which is pre-set, in a conventional method, at a value sufficiently higher than an average systolic blood-pressure value. Thus, the pain felt by the patient in blood-pressure measurement can be reduced.

While the present invention has been described in detail in its preferred embodiment, by reference to the drawings, the invention may otherwise be embodied.

For example, in the illustrated embodiment, the cuff 12 is worn on the ankle 14. However, the cuff 12 may be modified to be worn on a body portion of the patient other than the ankle; such as a femoral portion or an upper arm.

In addition, in the illustrated embodiment, the cuff-pressure changing means 50 slowly increases the cuff pressure Pc from the slow-pressure-increase start pressure PT1, pre-stored in the ROM 36, till the time when the mean blood-pressure value BP(MEAN) is determined by the mean-blood-pressure determining means 56. However, the cuff-pressure changing means 50 may be modified to slowly decrease the cuff pressure Pc. In the latter case, the cuff-pressure changing means 50 quickly increases the cuff pressure Pc up to a pre-set pressure-increase target pressure that is higher than an average mean blood-pressure value BP(MEAN) of the body portion on which the cuff 12 is worn, and is lower than an average systolic blood-pressure value BP(MEAN) of the body portion, and slowly decreases the cuff pressure Pc from the pressure-increase target pressure.

Moreover, in the illustrated embodiment, the cuff-pressure changing means 50, first, quickly increases the cuff pressure Pc up to the slow-pressure-increase start pressure PT1 pre-stored in the ROM 36, and then slowly increases the cuff pressure Pc. However, the cuff-pressure changing means 50 may be modified to slowly increase, from the beginning, the cuff pressure Pc.

Figure 7:
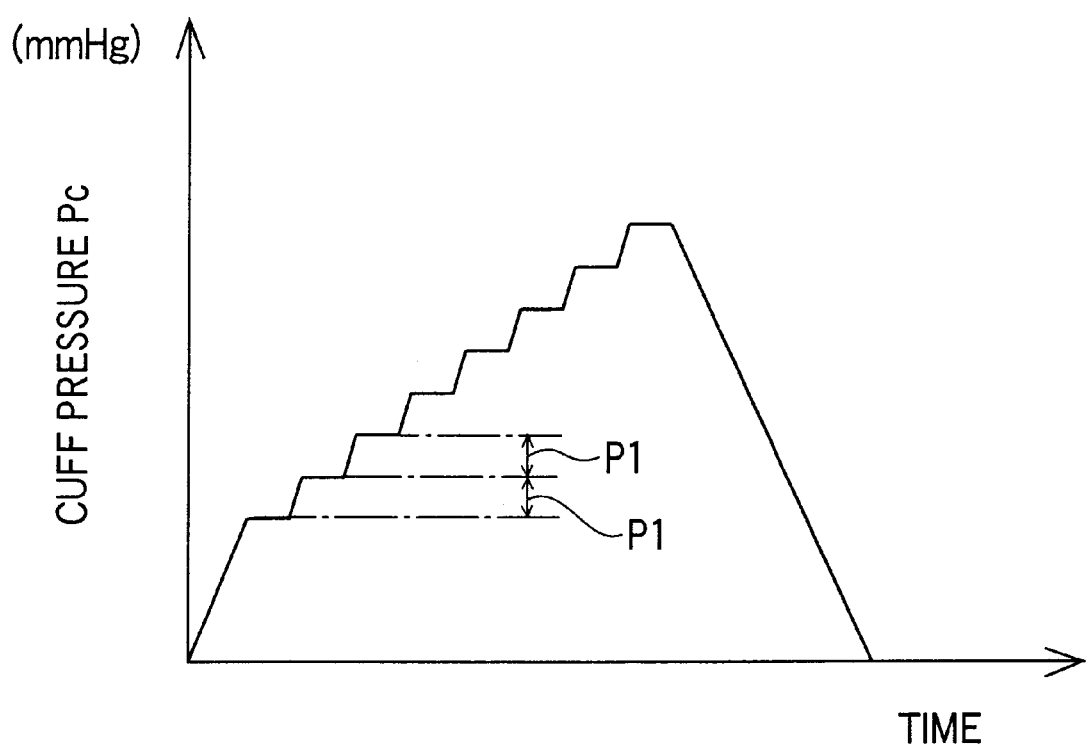
FIG. 7 is a time chart showing a manner, different from that shown in FIG. 3, in which the cuff-pressure changing means shown in FIG. 2 changes the cuff pressure Pc.

In addition, in the illustrated embodiment, the pulse-wave-magnitude determining means 58 determines the minimal magnitude Imin, etc. of the cuff pulse wave CW detected in the state in which the cuff pressure Pc is maintained at the pulse-wave-detect pressure PM lower than the diastolic, or mean, blood-pressure value BP(DIA) or BP(MEAN) by the cuff-pressure changing means 50. However, the pulse-wave-magnitude determining means 58 may be modified to determine the minimal magnitude Imin, etc. of the cuff pulse wave CW detected when the cuff pressure Pc is slowly increased. In the latter case, since the cuff pressure Pc is linearly increased as time elapses, the cuff pulse wave CW detected during the slow increasing of the cuff pressure Pc is influenced by the increasing of the cuff pressure Pc. To avoid this influence, the cuff pulse wave CW is corrected based on the prescribed low rate at which the cuff pressure Pc is slowly increased, and a minimal magnitude Imin, etc. of the thus corrected cuff pulse wave CW are determined. Alternatively, the cuff-pressure changing means 50 may be modified to slowly increase the cuff pressure Pc, step by step, each by a prescribed pressure, P1, as shown in FIG. 7. In this case, at each pressure step, the cuff pressure Pc is maintained for a time duration in which one or more heartbeat-synchronous pulses of the cuff pulse wave CW can be detected, and a minimal magnitude Imin, etc. of the thus detected cuff pulse wave CW are determined. Since the cuff pressure Pc is not changed during the cuff pulse wave CW is detected, it is not needed to correct the detected pulse wave CW.

In the present apparatus 10, a microphone may be provided in the cuff 12. In this case, the diastolic-blood-pressure determining means 54 may determine a diastolic blood-pressure value BP(DIA) of the patient based on a Korotkoff sound detected as a sort of heartbeat-synchronous signal by the microphone.

The present blood-pressure measuring apparatus 10 employs the blood-pressure re-determining means 62. However, for some applications, the accuracy (or reliability) of systolic blood-pressure values BP(SYS) determined by the systolic-blood-pressure determining means 60 may be sufficiently high. For those applications, the re-determining means 62 may be omitted.

According to the flow chart shown in FIG. 6, the control device 30 (S6) determines the diastolic blood-pressure value BP(DIA) of the patient based on the inflection point of the differentiated curve of the envelope of amplitudes A of the cuff pulse wave CW. However, the control device may determine a mean blood-pressure value BP(MEAN) of the patient based on the greatest amplitude A of the cuff pulse wave CW, and may determine a diastolic blood-pressure value BP(DIA) of the patient based on a series of amplitudes A obtained before the greatest amplitude A.

It is to be understood that the present invention may be embodied with other changes, improvements and modifications that may occur to a person skilled in the art without departing from the spirit and scope of the invention.

What is claimed is:

1. An apparatus for measuring a blood pressure of a living subject, comprising:

an inflatable cuff which is adapted to be worn on a body portion of the subject and which applies a pressure to the body portion of the subject;

a cuff-pressure changing device which changes the pressure of the cuff between a first pressure lower than a systolic blood pressure of the body portion of the subject and higher than a mean blood pressure of the body portion, and a second pressure lower than a diastolic blood pressure of the body portion;

a blood-pressure determining device which determines a diastolic blood pressure and a mean blood pressure of the subject based on a heartbeat-synchronous signal which is detected from the subject while the cuff-pressure changing device changes the pressure of the cuff;

a cuff-pulse-wave detecting device which detects a cuff pulse wave as an oscillation of the pressure of the cuff;

a pulse-wave-magnitude determining means for operating the cuff-pressure changing device to maintain the pressure of the cuff at a third pressure lower than the mean blood pressure of the body portion of the subject, and determining a minimal magnitude, a mean magnitude, and a maximal magnitude of the cuff pulse wave detected by the cuff-pulse-wave detecting device in a state in which the pressure of the cuff is maintained at the third pressure; and a systolic-blood-pressure determining means for determining a systolic blood pressure of the subject, based on the diastolic and mean blood pressure determined by the blood-pressure determining device and the minimal, mean, and maximal magnitudes of the cuff pulse wave determined by the pulse-wave-magnitude determining means, according to a fact that the minimal, mean, and maximal magnitudes of the cuff pulse wave correspond to the diastolic, mean, and systolic blood pressure of the subject, respectively.

2. An apparatus according to claim 1, wherein the cuff-pressure changing device increases the pressure of the cuff at a predetermined rate from a start pressure lower than the diastolic blood pressure of the body portion of the subject, and stops the increasing of the pressure of the cuff based on a fact that the blood-pressure determining device has determined the mean blood pressure of the subject.

3. An apparatus according to claim 1, further comprising a blood-pressure re-determining means for increasing the pressure of the cuff up to a target pressure higher by a predetermined pressure than the systolic blood pressure determined by the systolic-blood-pressure determining means, subsequently decreasing the cuff pressure at a pre-determined rate, and re-determining a systolic blood pressure of the subject based on the heartbeat-synchronous signal detected while the cuff pressure is decreased at the predetermined rate.

4. An apparatus according to claim 1, wherein the cuff pulse wave detected by the cuff-pulse-wave detecting device provides the heartbeat-synchronous signal detected from the subject while the cuff-pressure changing device changes the pressure of the cuff, and wherein the blood-pressure determining device determines the diastolic and mean blood pressure of the subject based on the cuff pulse wave detected by the cuff-pulse-wave detecting device.

5. An apparatus according to claim 1, further comprising a display device which displays at least one of the systolic blood pressure determined by the systolic-blood-pressure determining means and the systolic blood pressure determined by the blood-pressure re-determining means.

6. An apparatus according to claim 1, wherein the cuff-pressure changing device comprises:

an air pump which supplies a compressed air;

a pressure control valve which receives the compresses air from the air pump and controls the pressure of the cuff; and a control means for controlling the air pump and the pressure control valve to change the pressure of the cuff.

7. An apparatus according to claim 1, wherein the blood-pressure determining device comprises:

a pressure sensor which detects the pressure of the cuff that contains the oscillation as the cuff pulse wave;

a static-pressure filter circuit which extracts, from the cuff pressure containing the oscillation, a static pressure free of the oscillation; and a determining means for determining the diastolic and mean blood pressure of the subject based on the heartbeat-synchronous signal and the static pressure extracted by the static-pressure filter circuit.

8. An apparatus according to claim 7, wherein the cuff-pulse-wave detecting device comprises a pulse-wave filter circuit which extracts, from the cuff pressure containing the oscillation, the oscillation as the cuff pulse wave.

* * * * *